United States Patent [19]

Takayama

[11] 4,416,524
[45] Nov. 22, 1983

[54] LIGHT SOURCE DEVICE FOR AN ENDOSCOPE

[75] Inventor: Syuichi Takayama, Hachioji, Japan

[73] Assignee: Olympus Optical Co., Ltd., Tokyo, Japan

[21] Appl. No.: 370,087

[22] Filed: Apr. 20, 1982

Related U.S. Application Data

[63] Continuation of Ser. No. 193,649, Oct. 3, 1980, abandoned.

[30] Foreign Application Priority Data

Oct. 13, 1979 [JP] Japan .................. 54-132001

[51] Int. Cl.³ .............. G03B 15/05; G03B 29/00; A61B 1/06; H05B 41/14
[52] U.S. Cl. ....................... 354/31; 354/33; 354/62; 128/6; 315/151; 315/241 P
[58] Field of Search ................. 354/27, 31-35, 354/60 F, 62, 63, 79, 139, 145, 149; 128/6-9; 315/241 P, 151, 157, 159; 350/19; 351/7; 362/4

[56] References Cited

U.S. PATENT DOCUMENTS

| | | | |
|---|---|---|---|
| 3,601,022 | 8/1971 | Langnau | 354/34 |
| 3,626,827 | 12/1971 | Yanagi | 354/35 |
| 3,670,722 | 6/1972 | Kosaka | 128/6 |
| 4,192,597 | 3/1980 | Ting | 354/62 X |

*Primary Examiner*—William B. Perkey
*Attorney, Agent, or Firm*—Frishauf, Holtz, Goodman & Woodward

[57] ABSTRACT

A photoreceptor is provided directly for receiving a light emitted from an electronic flash unit, and an output of the photoreceptor is supplied to a light emission amount calculating circuit. The light emission amount calculating circuit includes a light emission amount calculating constant setting device adapted to manually change a light emission amount calculating constant according to a photographing mode.

8 Claims, 4 Drawing Figures

LIGHT SOURCE DEVICE FOR AN ENDOSCOPE

This is a continuation of application Ser. No. 193,649, filed Oct. 3, 1980, now abandoned.

BACKGROUND OF THE INVENTION

This invention relates to a light source device for an endoscope and in particular to a light source device using an electronic flash tube.

Recently, a light source device for an endoscope system which incorporates an electronic flash tube or a strobe tube therein has been developed. The amount of light emission of the strobe tube has to be changed according to a foreground subject, for example, a near- or far-distant subject. The amount of light emission is controlled by the following methods.

(1) A plurality of main capacitors are connected to the strobe tube and the number of main capacitors is selected according to the amount of light emission.

(2) A resistor is connected to the strobe tube, thereby adjusting a dissipation power of the strobe tube.

(3) The light emission time of the strobe tube is controlled by a timer.

In the first method (1), a number of main capacitors are required and, moreover, an elaborate and expensive switch is necessary for selecting these main capacitors. The second method (2) requires a plurality of larger-sized resistors, making the device bulkier. Furthermore, an elaborate switch is required for selecting these resistors. In the third method (3), since the light emission time of the strobe tube is very short, an amount of light varies greatly with a slight variation of a timer.

It is accordingly an object of this invention to provide an inexpensive, smaller-sized light source device for an endoscope which can readily effect an accurate light amount adjustment.

SUMMARY OF THE INVENTION

According to this invention a photoreceptor is provided for directly receiving some of the light from an electronic flash tube and for converting the directly received light into an electrical output. The electrical output signal of the photoreceptor is inputted to a light emission amount calculating circuit for calculating a light emission amount of the flash unit. A setting device is provided for manually setting a calculated constant of the calculating circuit and a light emission amount of the electronic flash unit is controlled according to the set amount of the setting device.

DETAILED DESCRIPTION

Figure 1:
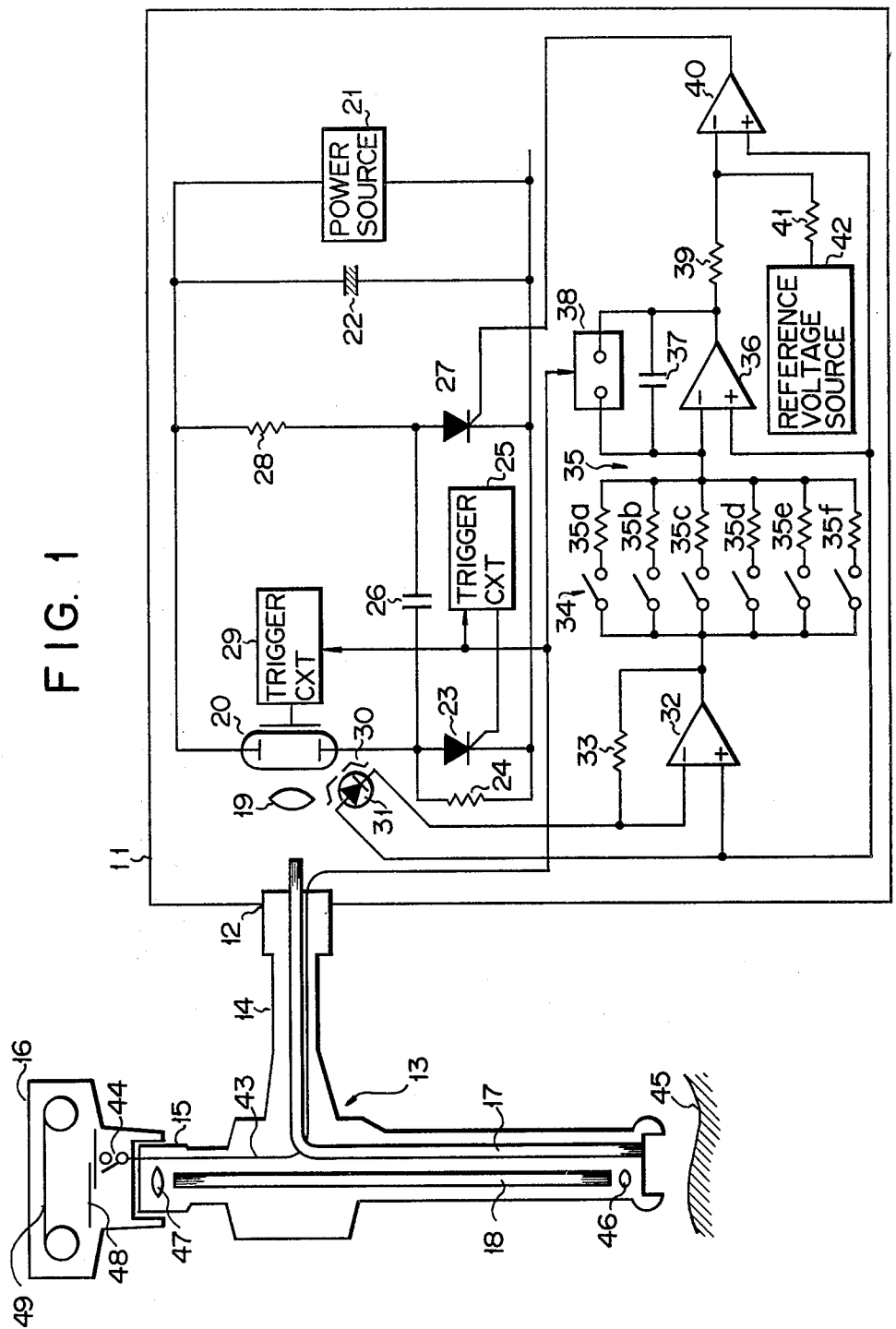
FIG. 1 shows a circuit diagram of a light source device according to one embodiment of this invention.

In FIG. 1 a cable 14 of an endoscope 13 is connected to a socket portion 12 of a light source device 11. An endoscope camera 16 is mounted on an eyepiece section 15 of the endoscope 13. The endoscope 13 includes a light guide 17 and image guide 18, and the light guide 17 extends into the light source device 11 through cable 14. An electronic flash unit including an electronic flash tube or a strobe tube 20 is disposed in the light source device 11 such that it is arranged opposite to the light incident end of the light guide 17 with a condenser lens 19 in between. The strobe tube 20 has one electrode connected to one end of a main capacitor 22 and the other electrode connected through the anode-to-cathode path of a main thyristor 23 to the other end of the main capacitor 22 which is connected in parallel with a power source circuit 21. A resistor 24 is connected between the anode and the cathode of the main thyristor 23. The anode of the main thyristor 23 is connected to the cathode of the main thyristor 23 through a commutation capacitor 26 and commutation thyristor 27. A trigger circuit 29 is connected to a trigger electrode of the strobe tube 20. Both ends of a photoreceptor, for example, the cathode and anode of a photodiode 31 are connected to inverting and noninverting input terminals, respectively, of an operational amplifier 32, the photodiode 31 being arranged near to the strobe tube 20 through a diaphragm or a stop 30. A resistor 33 is connected between the inverting input terminals and output terminal of the operational amplifier 32. The output terminal of the operational amplifier 32 is connected to an integrating circuit 35 through a light emission amount setting switch 34 of a light emission amount calculating circuit. The integrating circuit 35 comprises a plurality of resistors 35a, 35b, 35c, 35d, 35e and 35f which are selected by a light emission amount setting switch 34, an operational amplifier 36 whose inverting input terminal is connected to a common connecting point of these resistors, and a capacitor 37 connected in parallel between an output terminal and inverting input terminal of the operational amplifier 36. An electronic switch 38 is connected in parallel with the capacitor 37. The output terminal of the operational amplifier 36 is connected to an inverting input terminal of an operational amplifier 40 through a resistor 39. A reference voltage source 42 is connected through a resistor 41 to the inverting input terminal of the operational amplifier 40. The noninverting input terminals of the operational amplifiers 32, 36 and 40 are connected to the anode of the photodiode 31.

A synchro-contact 44 provided in the camera 16 is connected to the trigger circuits 25 and 29 and control input terminal of the electronic switch 38 in the light source device through a signal line which is provided in the endoscope 13.

When the power source 21 is closed, the main capacitor 22 and commutation capacitor 26 are charged. Suppose that at this time the resistor 35a is selected by the light emission amount setting switch 34. When in this state a release button (not shown) of the camera 16 is depressed and the synchro-contact 44 is closed, a shutter 48 is opened and the trigger circuits 25 and 29 are driven. As a result, a trigger signal is supplied to the trigger electrode of the strobe tube 20 and the gate electrode of the main thyristor 23 to cause the strobe tube to emit light, light emitted from the strobe tube 20 illuminates the subject 45 through the light guide 17 of the endoscope 13 and a light reflected from the subject exposes a film 49 through an objective lens 46, image guide 18, photographing lens 47 and opened shutter 48. The photodiode 31 directly receives some of the light emitted from the strobe tube 20 with the diaphragm 30 disposed therebetween to convert it to a photocurrent signal. The photocurrent signal is converted to a voltage signal by a current-voltage converter comprising the amplifier 32 and resistor 33, and inputted to the integrating circuit 35 where it is integrated to a photovoltage signal based on an integral time constant determined by the resistor 35b and capacitor 37. The output of the integrating circuit 35 is compared with the reference voltage of the reference voltage source 42. When the output of the integrating circuit 35 reaches a predetermined value, the output of the operational amplifier 40 is supplied as a trigger signal to the gate of the commutation thyristor 27. As a result, the commutation thyristor 27 is rendered conductive, causing the commutation capacitor 26 to reverse-bias the main thyristor 23 through the commutation thyristor 27 to permit the main thyristor 23 to be rendered nonconductive i.e. in the OFF state. As a result, the strobe tube stops its light emission.

As evident from the above, the integral time constant of the integrating circuit 35 is set to a desired value by selecting one of resistors 35a to 35f of the integrating circuit 35 by means of the light emission amount setting switch 34. By so doing, the light emission amount of the strobe tube is controlled. Suppose that the resistive values $R_1$, $R_2$, $R_3$, $R_4$, $R_5$ and $R_6$ of the resistors 35a, 35b, 35c, 35d, 35e, and 35f are $R_1=2R_2=4R_3=8R_4=16R_5=32R_6$. In this case, a light emission amount (strobe tube 20) for obtaining the same integrated voltage becomes one half for the resistor 35b and one fourth for the resistor 35c, provided that theresistive value $R_1$ of the resistor 35a is 1. Thus, the resistive values of the resistors correspond to light emission amounts.

Figure 2:
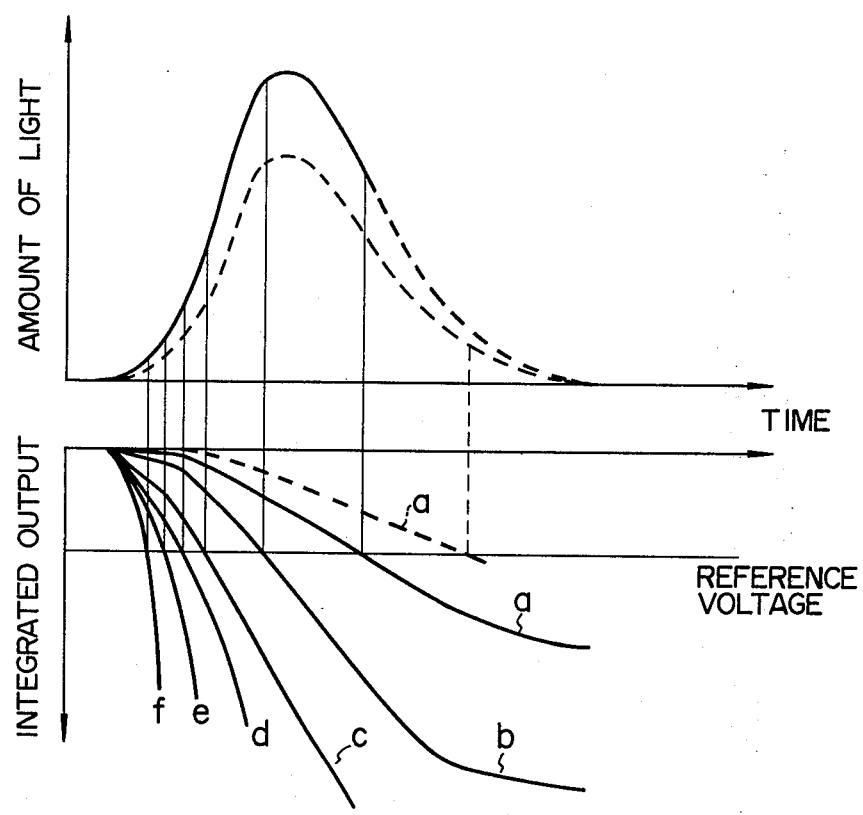
FIG. 2 is a curve for explaining a light amount control.

FIG. 2 shows an amount of light as obtained according to the integrated output. In FIG. 2 the curves a, b, c, d, e and f show integrated outputs as obtained from the resistors 35a, 35b, 35c, 35d, 35e, and 35f. It is to be noted that the broken lines of FIG. 2 show the integrated output and light amount when the power source voltage is lowered. If, for example, the resistor 35b is selected, a light amount as determined on an intersection of the corresponding curve b and reference voltage line is obtained. Therefore, the light emission amount of the strobe tube can be arbitrarily set by selecting one of the resistors 35a to 35f. It is to be noted, however, that it is unnecessary that the resistive values of the resistors 35a to 35f be set to have the above-mentioned relation.

Figure 3:
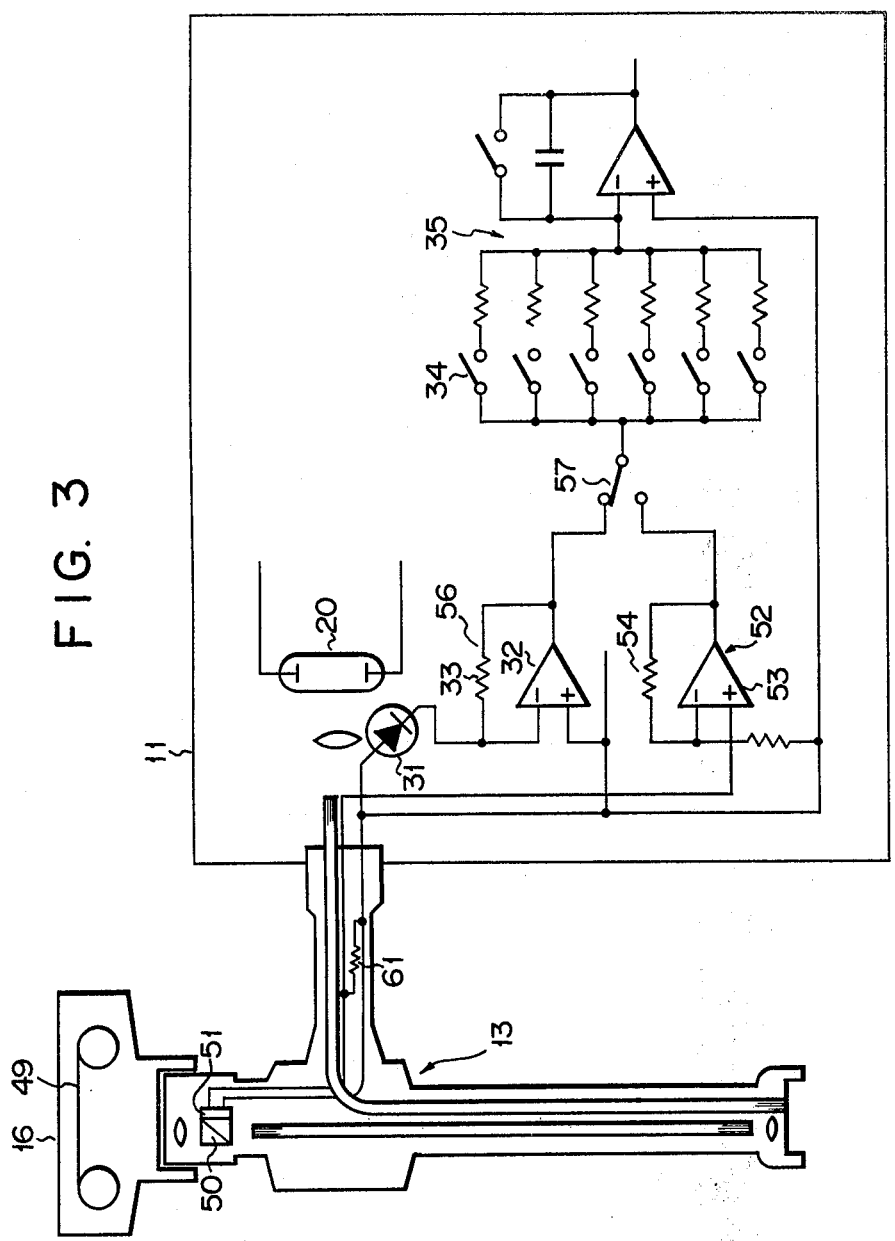
FIG. 3 shows part of a circuit diagram of a light source device according to another embodiment of this invention.

A light source device according to another embodiment of this invention will be explained below with reference to FIG. 3. In this embodiment, a photoreceptor 51 receives a reflection light split by a beam splitter 50 in the endoscope 13 and a photocurrent signal of the photoreceptor 51 is supplied to an amplifier circuit 52 in the light source device 11. The amplifier circuit 52 comprises an operational amplifier 53 and resistors 54 and 55 and converts the photocurrent to a voltage and amplifies it. The output terminals of the amplifier circuits 52 and 56 are connected to a light emission amount setting switch 34 through a changeover switch 57. The changeover switch 57 is provided to effect switching between an autoexposure and a manual exposure. In the case of an autoexposure the output of the amplifier circuit 52 is supplied to an integrating circuit 35 and in the case of the manual exposure the output of the amplifier circuit 56 is supplied to the integrating circuit 35. Since in the case of the autoexposure a light signal corresponding to a light by which a film 49 of the camera is directly exposed is integrated by the integrating circuit 35, an amount of exposure is automatically determined by an amount of light designated by the integral constant irrespective of the distance between the endoscope 13 and the subject 45. In the case of the autoexposure, a light signal corresponding to some of a light emitted from the strobe tube is integrated and it is therefore necessary to change an integral constant according to the subject. This embodiment permits a free choice of the autoexposure and manual exposure, improving a photographing function.

Figure 4:
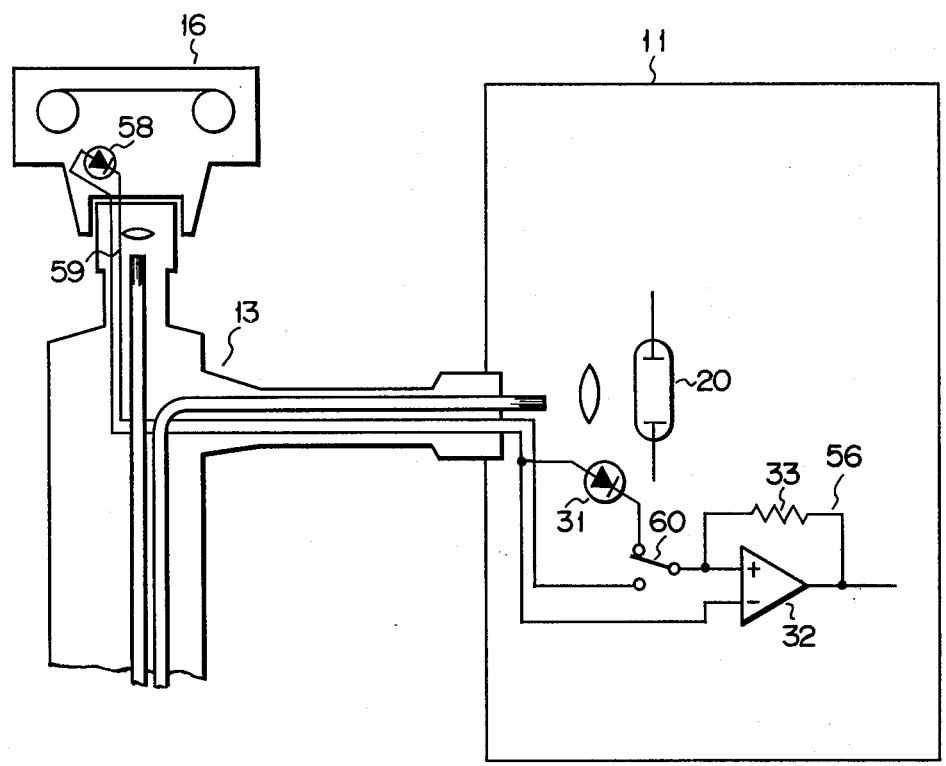
FIG. 4 shows a part of a circuit diagram of a light source device according to another embodiment of this invention.

In an embodiment shown in FIG. 4 a photoreceptor 58 measure a reflection light from a film in the camera. A light signal so measured is conducted through a signal line 59 to the light source device 11. A changeover switch 60 is provided in the light source device 11 and adapted to be connected to the photoreceptor 58 in the camera 16 and a photoreceptor 31 in the light source device. The changeover switch 60 selects either one of the photoreceptors 58 and 31 and supplies it to an amplifier circuit 56 so as to effect switching between the autoexposure and the manual exposure. That is, the autoexposure is made when a light signal of the photoreceptor 58 is supplied to the amplifier circuit 56 and the manual exposure is made when a light signal of the photoreceptor 31 is supplied to the amplifier circuit.

As is evident from the above-mentioned explanation, according to this invention a photoreceptor is provided for directly measuring a light emitted from the strobe tube and a light signal from the photoreceptor is integrated according to an integral constant manually set. When an integrated output reaches a predetermined value the light emission of the strobe tube is stopped. Therefore, an amount of light emission can be fairly accurately controlled by the mere setting of the integral constant and, even if a power source voltage varies, it is possible to obtain a predetermined controlled amount of light. Furthermore, since the photoreceptor is arranged near to the strobe tube, a light signal obtained has a greater level, thereby alleviating a drift in the integrating circuit and improving an integrating accuracy. In consequence, it is possible to effect a light amount control with higher accuracy. Even in the case of the manual exposure it is only necessary that the constant of the integrating circuit be switched. This makes the light source device compact in size and inexpensive.

What is claimed is:

1. A light source device for an endoscope having an endoscope camera coupled thereto, comprising:
   a source of power:
   an electronic flash unit coupled to said source of power for emitting light in response to a synchro-signal of an endoscope camera;
   means for directing light from said electronic flash unit to a subject to be photographed;
   a photoreceptor, disposed adjacent said electronic flash unit with a direct, unimpeded light path between the photoreceptor and said electronic flash unit, for directly receiving light from the electronic flash unit and for converting the directly received light into an electrical output signal which is a function of the amount of directly received light of the photoreceptor;
   a light emission amount calculating circuit connected to the photoreceptor for performing a calculation on said electrical output signal of said photoreceptor, said light emission amount calculating circuit including means for manually setting a calculation constant to obtain a desired substantially constant amount of light to be emitted by said electronic flash unit, and means for generating an output signal as a result of said calculation, which output signal corresponds to said desired substantially constant amount of light; and means coupled to said light emission amount calculating circuit and to said electronic flash unit for stopping a light emission of said electronic flash unit responsive to said output signal of said light emission amount calculating circuit to thereby emit said substantially constant amount of light irrespective of the distance to a subject or a lowering in emission efficiency of said electronic flash unit or a lowering in power source voltage.

2. A light source device according to claim 1, in which said light emission amount calculating circuit comprises selection switch means connected to the photoreceptor; a plurality of calculation constant setting resistors connected to said selection switch means; an integrating circuit connected to said resistors; and a comparator for comparing an output of said integrating circuit with a reference voltage and for generating said output signal of said light emission amount calculating circuit.

3. A light source device according to claim 1 or 2, further including receiving means for receiving an electrical signal corresponding to a light incident on said endoscope camera; and means for connecting one of an output of said receiving means and an output of said photoreceptor to said light emission amount calculating circuit.

4. A light source device according to claim 3, in which said endoscope has an eyepiece with a further photoreceptor therein for generating said electrical signal corresponding to a light incident on said endoscope camera.

5. A light source device according to claim 3, in which said endoscope camera includes a still further photoreceptor for outputting an electrical signal corresponding to a light incident on the camera; and means is provided for coupling an output of the still further photoreceptor to said receiving means.

6. A light source device according to claim 2, in which said calculation constant setting resistors are set such that they have different resistive values corresponding to the ascending powers of $\frac{1}{2}$.

7. A light source device according to claim 1 or 2, further comprising diaphragm means coupled between said electronic flash unit and said photoreceptor for reducing the amount of light incident on said photoreceptor.

8. A light source device according to claim 2, wherein said comparator generates said output signal of said light emission amount calculating circuit when the output of said integrating circuit is substantially equal to said reference voltage.

* * * * *

UNITED STATES PATENT AND TRADEMARK OFFICE
CERTIFICATE OF CORRECTION

PATENT NO. : 4,416,524

DATED : November 22, 1983

INVENTOR(S) : Syuichi TAKAYAMA

It is certified that error appears in the above-identified patent and that said Letters Patent is hereby corrected as shown below:

On the title page in the Abstract

Line 1, "provided directly for" should read

--provided for directly--;

Column 1, line 43, "electrical output" should read

--electrical output signal--.

Signed and Sealed this

Fifth Day of June 1984

[SEAL]

Attest:

GERALD J. MOSSINGHOFF

*Attesting Officer*   *Commissioner of Patents and Trademarks*